United States Patent [19]

Schaper et al.

[11] 4,232,178
[45] Nov. 4, 1980

[54] PROCESS FOR THE PREPARATION OF AN AROMATIC HYDROCARBON MIXTURE USING IRON CRYSTALLINE SILICATES

[75] Inventors: Lambert Schaper; Swan T. Sie, both of Amsterdam, Netherlands

[73] Assignee: Shell Oil Company, Houston, Tex.

[21] Appl. No.: 43,194

[22] Filed: May 29, 1979

[30] Foreign Application Priority Data

May 30, 1978 [NL] Netherlands ......................... 7805840

[51] Int. Cl.$^3$ .............................................. C07C 15/00
[52] U.S. Cl. .................................... 585/408; 585/409
[58] Field of Search ................................ 585/408, 409

[56] References Cited

U.S. PATENT DOCUMENTS 4,039,600  8/1977  Chang ................................... 585/408

FOREIGN PATENT DOCUMENTS 2628723  1/1977  Fed. Rep. of Germany .

Primary Examiner—Veronica O'Keefe
Attorney, Agent, or Firm—Ronald R. Reper

[57] ABSTRACT

A process is disclosed for the conversion of certain difficultly converted aliphatic oxygen-containing hydrocarbons to aromatic hydrocarbons by contacting them in low concentrations with certain other aliphatic oxygen-containing hydrocarbons over certain crystalline silicates containing iron in their structure.

7 Claims, No Drawings

PROCESS FOR THE PREPARATION OF AN AROMATIC HYDROCARBON MIXTURE USING IRON CRYSTALLINE SILICATES

The invention relates to a process for the preparation of an aromatic hydrocarbon mixture from a mixture of aliphatic compounds.

BACKGROUND OF THE INVENTION

Aromatic hydrocarbon mixtures are used on a large scale as gasoline. By distillation and extraction, individual aromatic compounds can be isolated from them such as benzene, toluene, the xylenes, and ethylbenzene which are used on a large scale as base materials for the chemical industry. Until recently, aromatic hydrocarbon mixtures suitable for the above-mentioned applications were prepared mainly by catalytic reforming of aliphatic hydrocarbon mixtures.

In an investigation concerning the preparation of aromatic hydrocarbon mixtures from aliphatic compounds, it was found that certain crystalline silicates which were recently synthesized for the first time, and described in Netherlands Patent Application No. 7,613,957 incorporated herein by reference, are suitable for use as catalyst for the preparation of aromatic hydrocarbon mixtures from aliphatic oxygen-containing hydrocarbons having the general formula $C_nH_mO_p$. By contacting a compound of this type at an elevated temperature with a catalyst containing one of these crystalline silicates, a hydrocarbon mixture is obtained which can be separated into a mixture of aliphatic hydrocarbons with from one to four carbon atoms in the molecule and an aromatic hydrocarbon mixture of which the components contain five and more carbon atoms in the molecule.

The suitability of a catalyst for the preparation of an aromatic hydrocarbon mixture from aliphatic oxygen-containing hydrocarbons having the general formula $C_nH_mO_p$ is judged by the activity and the selectivity which are defined as follows. Activity is a measure of the capacity of the catalyst to convert the compound $C_nH_mO_p$ into a mixture of hydrocarbons. The activity of the catalyst is higher according as more hydrocarbons are formed. Selectivity is a measure of the capacity of the catalyst to convert the compound $C_nH_mO_p$ into hydrocarbons with five and more carbon atoms in the molecule. The selectivity of the catalyst is expressed as the weight percentage of produced hydrocarbons with five and more carbon atoms in the molecule calculated on the total amount of hydrocarbons produced. A catalyst is judged to be more suitable for the preparation of an aromatic hydrocarbon mixture from aliphatic oxygen-containing hydrocarbons having the general formula $C_nH_mO_p$ according as activity and selectivity are higher.

Continued investigation concerning this subject by the applicant has shown that the use of the crystalline silicates for the present purpose using certain oxygen-containing hydrocarbons as the starting material yields much better results than when use is made of other oxygen-containing hydrocarbons, in spite of the fact that they will satisfy the above-mentioned general formula. It has been found that oxygen-containing hydrocarbons having the general formula $C_nH_mO_p$ can, according to their behavior in the conversion into an aromatic hydrocarbon mixture in the presence of crystalline silicates as the catalyst, be divided into two groups, namely compounds for which $m-2p/n$ is greater than 1 and compounds for which $m-2p/n$ is at most 1. When the crystalline silicates are used as catalysts in the conversion of compounds for which $m-2p/n$ is greater than 1, these catalysts show a high activity and selectivity. When the crystalline silicates are used as catalysts in the conversion of compounds for which $m-2p/n$ is at most 1, these catalysts show so low an activity that they are unsuitable for use in the conversion of these compounds on a technical scale.

Surprisingly, it has now been found that the crystalline silicates can nevertheless be used successfully as catalysts in the preparation of an aromatic mixture from the compounds for which $m-2p/n$ is at most 1 if these compounds are mixed with a predominant molar amount of one or more of the compounds for which $m-2p/n$ is at most 1. It has been found that when the crystalline silicates are used as catalysts for the preparation of an aromatic hydrocarbon mixture from the above mixtures of the two types of oxygen-containing hydrocarbons, the catalyst shows a high activity and selectivity.

SUMMARY OF THE INVENTION

The present patent application therefore relates to a process for the preparation of an aromatic hydrocarbon mixture from a mixture of aliphatic compounds which comprises contacting in a reaction zone as feed, a mixture of aliphatic oxygen-containing hydrocarbons having the general formula $C_nH_mO_p$, which mixture consists of a predominant molar amount of one or more compounds for which $m-2p/n$ is greater than 1, and the rest of one or more compounds for which $m-2p/n$ is at most 1 at an elevated temperature of from 250° to 650° C., with a catalyst containing a crystalline silicate, which (a) is thermally stable to temperatures above 600° C., (b) after dehydration at 400° C. in vacuum, is capable of adsorbing more than 3%w water at 25° C. and saturated water vapour pressure, and (c) in dehydrated form, has the following overall composition expressed in moles of the oxides:

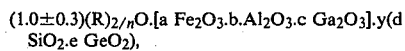

$(1.0\pm0.3)(R)_{2/n}O.[a\ Fe_2O_3.b.Al_2O_3.c\ Ga_2O_3].y(d\ SiO_2.e\ GeO_2)$, where:
R = one or more mono or bivalent cations,
$a \geq 0.1$,
$b \geq 0$,
$c \geq 0$,
$a+b+c=1$,
$y \geq 10$,
$d \geq 0.1$,
$e \geq 0$,
$d+e=1$,
n = the valency of R, and withdrawing an aromatic hydrocarbon product from said reaction zone.

DESCRIPTION OF PREFERRED EMBODIMENTS

The new crystalline silicates which have the property of catalyzing the above-mentioned conversion have the following characteristics:

(a) They are thermally stable to temperatures above 600° C.

(b) After dehydration at 400° C. in vacuum, they are capable of adsorbing more than 3%w water at 25° C. and saturated water vapour pressure.

(c) In dehydrated form, they have the following overall composition expressed in moles of the oxides:

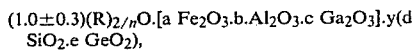

$(1.0\pm0.3)(R)_{2/n}O.[a\ Fe_2O_3.b.Al_2O_3.c\ Ga_2O_3].y(d\ SiO_2.e\ GeO_2)$, where:
R = one or more mono or bivalent cations,
$a \geq 0.1$,
$b \geq 0$,
$c \geq 0$,
$a+b+c = 1$,
$y \geq 10$,
$d \geq 0.1$,
$e \geq 0$,
$d+e = 1$, and
n = the valency of R.

Examples of aliphatic oxygen-containing hydrocarbons having the general formula $C_nH_mO_p$ for which $m-2p/n$ is greater than 1 and which are suitable for use in a predominant molar amount in the starting mixtures according to the invention are monovalent alcohols, ethers, ketones, and aldehydes with at least three carbon atoms in the molecule. Examples of aliphatic oxygen-containing hydrocarbons having the general formula $C_nH_mO_p$ for which $m-2p/n$ is most 1 and which are suitable for use in a minor molar amount in the starting mixtures according to the invention are carboxylic acids, polyvalent alcohols, carbohydrates, carboxylic anhydrides, and aldehydes with less than three carbon atoms in the molecule. A very suitable starting mixture for the process according to the invention consists of a predominant molar amount of a monovalent alcohol and the rest of a monocarboxylic acid. A particularly preferred starting mixture is one which consists of a predominant molar amount of methanol and the rest of acetic acid.

In the process according to the invention, the compounds for which $m-2p/n$ is greater than 1 and the compounds for which $m-2p/n$ is at most 1 should be present in a molar ratio which is greater than 1. This molar ratio is preferably carried out at a temperature of from 250° to 650° C. and, in particular of from 300° to 500° C., a pressure of from 1 to 200 bar and a space velocity of from 0.1 to 10 $1.1^{-1}.h^{-1}$. The process according to the invention may be started from a mixture which contains only one compound for which $m-2p/n$ is greater than 1 and the compounds for which $m-2p/n$ is at most 1 but mixtures in which several compounds from each of the two groups are present can also very suitably be used. Such mixtures of oxygen-containing hydrocarbons may be prepared, for instance, by controlled partial oxidation of hydrocarbons or hydrocarbon mixtures such as propane, butane, or naphtha in the vapor or in the liquid phase. Suitable mixtures of oxygen-containing hydrocarbons may also be prepared according to Fischer-Tropsch from mixtures of carbon monoxide and hydrogen.

As previously mentioned, the process according to the invention is preferably started from a mixture of methanol and acetic acid. Particularly preferred are mixtures of methanol and acetic acid which have been obtained by conversion of methanol with carbon monoxide in the presence of a carbonylation catalyst. The carbonylation reaction is preferably carried out at a temperature of from 150° to 425° C. and a pressure of from 1 to 70 bar. Further, the carbonylation reaction is preferably carried out to the point at which the molar ratio of methanol to acetic acid in the product is at least 12:1. Suitable catalysts for carrying out the carbonylation are phosphoric acid and boron trifluoride. A preferred catalyst is one which contains rhodium, in particular, such a catalyst which contains, in addition, iodine as the promoter. The mixture of methanol and carbon monoxide that serves as the feed for the carbonylation reaction for the preparation of a mixture of methanol and acetic acid is preferably obtained by reacting carbon monoxide and hydrogen in the presence of a methanol synthesis catalyst, in particular, a catalyst containing zinc and/or copper. This methanol synthesis is preferably carried out at a temperature of from 200° to 400° C. and a pressure of from 25 to 425 bar. The mixture of carbon monoxide and hydrogen that serves as the feed for the methanol synthesis may very conveniently have been prepared by gasification of carbon-containing materials such as brown coal, anthracite, coke, crude mineral oil and fractions thereof, and oils recovered from tar sand and bituminous shale. Suitable mixtures of carbon monoxide and hydrogen can also be prepared by steam reforming and/or partial oxidation of natural gas. If the process according to the invention is carried out as part of the integrated process described above, the yield of hydrocarbons with five and more carbon atoms in the molecule can be increased further by separating unconverted carbon monoxide and $C_4$-hydrocarbons formed in the reaction in the presence of the crystalline silicate from the aromatic reaction product and using them again in the process; the carbon monoxide as the feed component in the methanol synthesis and the $C_4$-hydrocarbons formed in the reaction in the presence of the crystalline silicate from the aromatic reaction product and using them again in the process; the carbon monoxide as the feed component in the methanol synthesis and the $C_4$-hydrocarbons as the feed components in the preparation of the mixture of carbon monoxide and hydrogen.

In the process according to the invention, it is preferred to use crystalline silicates in which no gallium or germanium are present. In other words, silicates of which, in the above-mentioned overall composition, c and e are 0. Such silicates are the subject of Netherlands Patent Application No. 7,613,957. Further, it is preferred to use silicates of which, in the above-mentioned overall composition, a is at least 0.5. It should be noted that in the silicates used in the process according to the invention, y is preferably less than 600 and, in particular, less than 300. Finally, it is preferred in the process according to the invention to use silicates whose x-ray powder diffraction pattern has, inter alia, the reflections given in Table A of Netherlands Patent Application No. 7,613,957.

The crystalline silicates which are used as the catalyst in the process according to the invention are usually prepared starting from an aqueous mixture containing the following compounds in a certain ratio: one or more compounds of an alkali metal; one or more compounds that comprise an organic cation of from which such a cation is formed during the preparation of the silicate; one or more silicon compounds; one or more iron compounds; and, optionally, one or more aluminum, gallium, and/or germanium compounds. The preparation is carried out by maintaining the mixture at an elevated temperature until the silicate has been formed and then separating the crystals of the silicate from the mother liquor. Before being used in the process according to the invention, the organic cations introduced during the preparation should be converted into hydrogen ions by calcination. It is preferred to use in the process silicates whose alkali metal content is less than 1%w and, in particular, less than 0.05%w. Such silicates can be prepared from the above-mentioned calcined silicates by ion exchange, for instance, with an aqueous solution of an ammonium salt followed by calcination.

The invention will now be further explained with reference to the following example.

EXAMPLE

A crystalline iron-aluminum silicate (silicate A) was prepared as follows: a mixture of $Fe(NO_3)_3$, $Al(NO_3)_3$, $SiO_2$, $NaNO_3$, and $[(C_3H_7)_4N]OH$ in water with the molar composition $Na_2O.4.5[(C_3H_7)_4N]_2O$. 0.5 $Al_2O_3$.0.5 $Fe_2O_3$.29.1 $SiO_2$. 428 $H_2O$ was heated in an autoclave at 150° C. under autogenous pressure for 48 hours. After the reaction mixture had cooled down, the silicate formed was filtered off, washed with water until the pH of the washed water was about 8, and dried for two hours at 120° C. Silicate A, thus prepared, had the following chemical composition: $0.86[(C_3H_7)_4]_2O$. 0.3 $Na_2O$. 0.55 $Fe_2O_3$. 0.45$Al_2O_3$. 32 $SiO_2$. 8$H_2O$. The silicate had an x-ray powder diffraction pattern substantially as given in Table B of Netherlands Patent Application No. 7,613,957. The silicate was thermally stable up to temperatures higher than 1,000° C. and was capable, after dehydration at 400° C. in vacuum, of adsorbing 7.8%w water at 25° C. and saturated water vapor pressure. With silicate A as the starting material, silicate B was prepared by successively calcining silicate A at 500° C., boiling with 1.0 molar $NH_4NO_3$ solution, washing with water, boiling again with 1.0 molar $NH_4NO_3$ solution and washing, drying at 120° C., and calcining at 500° C.

Three experiments were carried out in which methanol, acetic acid, and a 5:1 molar mixture of methanol and acetic acid were contacted with silicate B as the catalyst at a temperature of 375° C., a pressure of 3 bar and a space velocity of 0.67 $1.1^{-1}.h^1$. The results of these experiments are given in the following table:

|  | EXPERIMENT NUMBER | | |
| --- | --- | --- | --- |
|  | 1 | 2 | 3 |
| FEED | METHANOL | METHANOL/ACETIC ACID MIXTURE | ACETIC ACID |
| PART OF THE FEED CONVERTED INTO HYDROCARBONS | | | |
| %w methanol | 98 | 88 | — |
| %w acetic acid | — | 45 | 0.5 |
| COMPOSITION OF THE PRODUCT, %w ON $C_1^+$ | | | |
| $C_1$ | 2 | 2 | product |
| $C_2$ | 1 | 14 | was |
| $C_3$ | 7 | 8 | not |
| $C_4$ | 8 | 3 | analyzed |
| $C_{5-12}$ | 82 | 73 | |

What is claimed is:

1. A process for the preparation of an aromatic hydrocarbon mixture from a mixture of aliphatic compounds which comprises contacting in a reaction zone as feed, a mixture of aliphatic oxygen-containing hydrocarbons having the general formula $C_nH_mO_p$, which mixture consists of a predominant molar amount of one or more compounds selected from monovalent alcohols, ethers, ketones, and aldehydes with at least three carbon atoms in the molecule for which $m-2p/n$ is greater than 1 and the rest of the feed comprises a minor molar amount of one or more compounds selected from carboxylic acids, polyvalent alcohols, carbohydrates, carboxylic anhydrides, and aldehydes with less than three carbon atoms in the molecule for which $m-2p/n$ is at most 1 at an elevated temperature of from 250° to 650° C., with an aromatization catalyst comprising a crystalline silicate, which (a) is thermally stable to temperatures above 600° C.,
(b) after dehydration at 400° C. in vacuum, is capable of adsorbing more than 3%w water at 25° C. and saturated water vapour pressure, and
(c) in dehydrated form, has the following overall composition expressed in moles of the oxides:

$(1.0\pm0.3)(R)_{2/n}O.[a\ Fe_2O_3.b.Al_2O_3.c\ Ga_2O_3]. y(d\ SiO_2.e\ GeO_2)$, where:
R = one or more mono or bivalent cations,
$a \geq 0.5$
$b \geq 0$,
$c \geq 0$,
$a+b+c=1$,
$y \geq 10$,
$d \geq 0.1$,
$e \geq 0$,
$d+e=1$,
n = the valency of R, and withdrawing a hydrocarbon product from said reaction zone which product can be separated into a mixture of aliphatic hydrocarbons with one to four carbon atoms in the molecule and a hydrocarbon mixture of five or more carbon atoms in the molecule containing aromatic hydrocarbons.

2. A process according to claim 1 in the feed mixture of aliphatic oxygen-containing hydrocarbons the molar ratio of the compounds for which $m-2p/n$ is greater than 1 in respect of the compounds for which $m-2p/n$ is at most 1 is more than 2.

3. A process according to claim 1 wherein the contacting is at a temperature of from 300° to 500° C., a pressure of from 1 to 200 bar, and a space velocity of from 0.1 to 10 $1.1^{-1}.h^{-1}$.

4. A process according to claim 1 wherein the mixture of aliphatic oxygen-containing compounds consists of a predominant molar amount of a monovalent alcohol and the rest of said mixture of a monocarboxylic acid.

5. A process according to claim 4 wherein the mixture of aliphatic oxygen-containing compounds contains as the monovalent alcohol methanol and as the monocarboxylic acid acetic acid.

6. A process according to claim 1 wherein a crystalline silicate is used with an alkali metal content of less than 1%w.

7. A process according to claim 1 wherein a crystalline silicate is used of which, in the formula giving the overall composition, c and e are equal to 0.

* * * * *